(12) United States Patent
Gitter et al.

(10) Patent No.: US 8,956,648 B2
(45) Date of Patent: Feb. 17, 2015

(54) CALCIUMPHOSPHATE-BASED NANOPARTICLES AS CARRIER-SYSTEMS FOR PHOTODYNAMIC THERAPY

(75) Inventors: Burkhard Gitter, Jena (DE); Susanna Gräfe, Jena (DE); Arno Wiehe, Berlin (DE); Volker Albrecht, Nuthetal (DE); Matthias Epple, Hattingen (DE); Janine Schwiertz, Mülheim (DE); Kathirvel Ganesan, Tamil Nadu (IN)

(73) Assignee: Biolitec PharmaMarketing Ltd, F.T. Labuan (MY)

( * ) Notice: Subject to any disclaimer, the term of this patent is extended or adjusted under 35 U.S.C. 154(b) by 35 days.

(21) Appl. No.: 13/140,855

(22) PCT Filed: Dec. 18, 2009

(86) PCT No.: PCT/EP2009/009142
§ 371 (c)(1),
(2), (4) Date: Jun. 20, 2011

(87) PCT Pub. No.: WO2010/078941
PCT Pub. Date: Jul. 15, 2010

(65) Prior Publication Data
US 2011/0257586 A1    Oct. 20, 2011

(30) Foreign Application Priority Data
Dec. 19, 2008 (EP) .................. 08022155

(51) Int. Cl.
*A61P 35/00* (2006.01)
*A61P 31/04* (2006.01)
*A61K 9/14* (2006.01)
*A61K 31/5415* (2006.01)
*B82Y 5/00* (2011.01)
*A61K 9/51* (2006.01)
*A61K 41/00* (2006.01)
*A61K 49/00* (2006.01)

(52) U.S. Cl.
CPC .......... *A61K 9/5115* (2013.01); *A61K 41/0057* (2013.01); *A61K 49/0093* (2013.01); *A61K 41/0071* (2013.01); *Y10S 977/773* (2013.01)
USPC ......... 424/458; 604/20; 424/489; 514/410; 514/224.8; 514/80; 977/773

(58) Field of Classification Search
None
See application file for complete search history.

(56) References Cited

U.S. PATENT DOCUMENTS

| 8,207,211 B2 * | 6/2012 | Wharton et al. ............... 514/410 |
| 2007/0218049 A1 * | 9/2007 | Chen et al. ................. 424/130.1 |
| 2010/0323022 A1 * | 12/2010 | Hashimoto et al. ........... 424/489 |

OTHER PUBLICATIONS

Kawakami et al. "Spectrophotometric Determination of Alkaline Phosphatase and a-Fetoprotein in Human Serum with teach 5,10,15,20-tetrakis(4-phosphonooxyphenyl)porphine" Analyst, Feb. 1995, vol. 120 pp. 539-542.*
Wang, Haibo "Hydroxyapatite Degradation and Biocompatibility" Dissertation Ohio State University 2004.*

* cited by examiner

*Primary Examiner* — Robert A Wax
*Assistant Examiner* — Danah Al-Awadi
(74) *Attorney, Agent, or Firm* — Bolesh J. Skutnik; RJ Associates

(57) ABSTRACT

The present invention provides pharmaceutical photosensitizer-loaded nanoparticle formulations and their methods of preparation for photodynamic therapy, comprising a hydrophobic or hydrophilic photosensitizer, nanoparticulate calcium phosphate and in certain cases auxiliary reagents such as stabilizers. The calcium phosphate-based nanoparticle formulations of the present invention provide excellent storage stability and therapeutically effective amounts of photosensitizer for intravenous or topical administration. In a preferred embodiment, tetrapyrrole derivatives such as porphyrins, chlorins and bacteriochlorins, are the preferred hydrophobic photosensitizers to be formulated in calcium phosphate nanoparticle formulations for photodynamic tumor therapy. Additionally, 5,10,15,20-tetrakis(4-phosphonooxyphenyl)porphine (pTPPP) is a preferred hydrophilic photosensitizer for photodynamic tumor therapy. In another preferred embodiment, hydrophilic cationic and anionic photosensitizers, especially those of the phenazinium, phenothiazinium and xanthenes series have been found to inactive pathogen bacteria and are the preferred photosensitizers to be formulated in calcium phosphate nanoparticle formulations for antibacterial photodynamic therapy. In another embodiment, photosensitizing nanoparticle formulations are useful to locate cells, tissues or bacteria by using fluorescence imaging methods.

26 Claims, 10 Drawing Sheets

CALCIUMPHOSPHATE-BASED NANOPARTICLES AS CARRIER-SYSTEMS FOR PHOTODYNAMIC THERAPY

NATIONAL FILING UNDER 35 USC 371

This application is being filed as a US National stage under 35 USC 371 of PCT Application No. PCT/EP09/09142 which was filed Dec. 18, 2009 and also claims the benefit of European Application Serial No. 08022155.9 filed Dec. 19, 2008, both of which are incorporated by reference herein.

BACKGROUND OF THE INVENTION

1. Field of the Invention

The present invention concerns the preparation of nanoparticle formulations containing hydrophobic or hydrophilic photosensitizers and their use in photodynamic therapy, particularly for tumor and antibacterial therapy, using intravenous or topical administration.

2. Invention Disclosure Statement

Calcium phosphate nanoparticles have gained increasing interest in recent years due to their high biocompatibility which is due to the fact that calcium phosphate constitutes the inorganic mineral of mammalian bone and teeth (S. V. Dorozhkin, M. Epple, Angew. Chem., Int. Ed., 2002, 41, 3130-3146; M. Vallet-Regi, Dalton Trans., 2006, 5211-5220; C. Rey, C. Combes, C. Drouet, H. Sfihi, A. Barroug, Mater. Sci. Eng., C, 2007, 27, 198-5220). Calcium phosphate nanoparticles can also act as drug carriers, e.g. for nucleic acids (V. Sokolova, M. Epple, Angew. Chem. Int. Ed., 2008, 47, 1382-1395) or for antitumor drugs (B. Palazzo. M. Iafisco, M. Laforgia, N. Margiotta, G. Natile, C. L. Bianchi, D. Walsh, S. Mann, N. Roveri, Adv. Funct. Mater., 2007, 17, 2180-2188; E. Boanini, M. Gazzano, K. Rubini, A. Bigi, Adv. Mater., 2007, 19, 2499-2502; X. Cheng, L. Kuhn, Int. J. Nanomed. 2007, 2, 667-674). For instance, a successful cell transfection was achieved with DNA- and siRNA-coated calcium phosphate nanoparticles (A. Maitra, Exp. Rev. Mol, Diagn., 2005, 5, 893-905; Y. Kakizawa, S. Furukawa, A. Ishii, K. Kataoka, J. Controlled Release, 2006, 111, 368-370; V. V. Sokolova, I. Radtke, R. Heumann, M. Epple, Biomaterials, 2006, 27, 3147-3153; D. Olton, J. Li, M. E. Wilson, T. Rogers, J. Close, L. Huang, N. P. Kumta, C. Sfeir, Biomaterials, 2007, 28, 1267-1279; V. Sokolova, A. Kovtun, O. Prymak, W. Meyer-Zaika, E. A. Kubareva, E. A. Romanova, T. S. Oretskaya, R. Heumann, M. Epple, J. Mater. Chem., 2007, 17, 721-727). Another example is disclosed in the Patent N° US 2008/0241256 A1 by Kuhn. Here calcium phosphate nanoparticle active agent conjugates suitable for targeting active agent delivery to tumor cells and lymphatics for the treatment of cancer and the treatment or prevention of cancer metastasis are described. Even though the enhanced drug delivery system may provide many advantages over prior art formulations, the anticancer drugs adsorbed onto calcium phosphate nanoparticles are either chemotherapeutic or releasing hormone agonists which may have numerous serious side effects, because they interfere with normal cell growth as well as cancer cell growth.

Inorganic nanoparticles exhibit various advantages towards organic nanoparticles: They are not attacked by microbial strains, they are frequently non-toxic, the preparation is easy and the storage stability is commonly good. (V. Sokolova, M. Epple, Angew. Chem., Int. Ed., 2008, 47, 1382-1395). Especially calcium phosphate nanoparticles fulfill all these advantages, because they are both biodegradable and biocompatible (D. Tadic, F. Beckmann, K. Schwarz, M. Epple, Biomaterials 2004, 47, 3335-3340; C. Schiller, M. Epple, Biomaterials 2003, 24, 2037-2043: D. Tadic, F. Peters, M. Epple, Biomaterials 2002, 23, 2553-2559; S. V. Dorozhkin, M. Epple, Angew. Chem. Int. Ed. 2002, 41, 3130-3146). In addition, they are structurally and chemically very close to the mineral in human bone (S. Weiner, H. D. Wagner, Annu. Rev. Mater. Sci. 1998, 28, 271-298). Another benefit of calcium phosphate nanoparticles is the possibility to incorporate lanthanides. These lanthanide-doped particles show fluorescence therefore it is easily possible to track the pathway through e.g. cells. (A. Doat, M. Fanjul, F. Pelle, E. Hollande, A. Lebugle, Biomaterials 2003, 24, 3365-3371; A. Doat, F. Pelle, N. Gardant, A. Lebugle, J. Solid State Chem. 2004, 177, 1179-1187; A. Lebugle, F. Pelle, C. Charvillat, I. Rousselot, J. Y. Chane-Ching, Chem. Commun. 2006, 606-608; S. Padilla Mondejar, A. Kovtun, M. Epple, J. Mater. Chem. 2007, 17, 4153-4159; V. Sokolova, A. Kovtun, R. Heumann, M. Epple, J. Biol. Inorg. Chem. 2007, 12, 174-179).

Photodynamic therapy (PDT) is a promising technique being explored for use in a variety of medical applications and is known as a well-recognized treatment for the destruction of tumors (T. D. Mody, J. Porphyrins Phthalocyanines, 2000, 4, 362-367). Photodynamic therapy uses light and a photosensitizer (a dye) to achieve its desired medical effect. A large number of naturally occurring and synthetic dyes have been evaluated as potential photosensitizers for photodynamic therapy. Perhaps the most widely studied class of photosensitizers are the tetrapyrrolic macrocyclic compounds. Among them, especially porphyrins and chlorins have been tested for their PDT efficacy.

Nevertheless, many photosensitizer formulations do not have chemical, pharmacological and/or photo-physical properties to improve the bioavailability and hence the effectiveness of the photosensitizer to achieve an effective PDT treatment.

Thus, many attempts have been made to improve the photosensitizer bioavailability by altering its pharmacokinetic and biodistribution. Providing organic nanoparticles as drug carriers, Patent N° US 2004/0047913 A1 by Allemann et al. discloses nanoparticle photosensitizers comprising green porphyrins and nanoparticles selected from polyester polymers such as poly(D,L-lactide-co-glycolide) and poly(D,L-lactide). Nevertheless, as previously mentioned organic nanoparticles have shown to exhibit various disadvantages compared to inorganic nanoparticles. Moreover, biodegradable polymer-based drug delivery carriers can often form polymer acidic byproducts or degrade into fragments that may modify the environment where the active agent is being release and may adversely affect the drug and/or the tissue they interact with.

Another photosensitizer formulation comprising luminescent nanoparticles with attached photosensitizers for PDT applications is disclosed in Patent N° US 2007/0218049 A1 by Chen et al. Upon exposure to ionizing radiation emitted by X-rays, alpha particles, beta particles, neutrons and gamma rays, luminescent nanoparticles emit light to activate the photosensitizers, which in turn produce a PDT killing effect in cancer cells. As luminescent nanoparticles need to be exposed to an ionizing radiation source the important advantage of high selectivity to killing tumor cells with minimal damage to surrounding tissue in PDT is lost. Even though, the killing effect in cancer cells is amplified by activation of the photosensitizer, healthy tissue such as skin or organs which ionizing radiation must pass through in order to treat the tumor is subjected to the hazardous effect of ionizing radiation.

Most substances successfully employed for photodynamic tumor therapy are lipophilic substances, which due to their inherent low solubility in water need to be formulated in a proper way to enhance their uptake and bioavailability. Highly hydrophilic substances on the other hand cannot be used for photodynamic tumor therapy as they do not sufficiently accumulate in the tumor tissue.

Another possible application of PDT is the treatment of infectious diseases caused by pathogenic microorganisms (M. Wainwright, Photodiagn. Photodyn. Ther., 2005, 2, 263-272). A constant problem in the treatment of infectious diseases is the lack of specificity of the agents used for the treatment of these diseases. Secondly, microorganisms can adapt and thus negate the effect of most chemically designed antimicrobials creating resistant strains, which require ever more active ingredients to stop their activity. In this respect PDT has been identified as a promising alternative as due to its different mode of action. In addition, there is only a very low possibility for the formation of resistant bacterial strains.

The use of PDT for the treatment of various types of disease has been limited due to the inherent features of photosensitizers (PS). These have included their high cost, extended retention in the host organism, substantial skin photo toxicity, low solubility in physiological solutions (which also reduces its usefulness for intravascular administration as it can provoke thromboembolic accidents), and low targeting effectiveness. These disadvantages, particularly of PS in the prior art, had led to the administration of very high doses of a photosensitizer, which dramatically increase the possibility of accumulation of the photosensitizer in non-damaged tissues and the accompanying risk of affecting non-damaged sites.

Efforts to reduce cost and to decrease background toxicity have been underway but are unrelated to the developments of the present invention. Work to improve solubility in physiological solutions, effects of skin photo toxicity, retention in host organism and to a lesser extent targeting effectiveness are the areas where the present invention provides new and non-obvious improvements on the use of PDT to treat various hyperplasia and related diseases as well as bacterial infections. Moreover, since the application of photodynamic therapy in the treatment of cancer and other diseases is increasing rapidly, there is also a bigger demand for new photosensitizer formulations. These new photosensitizer formulations need to be stable, easy to manufacture and to handle.

OBJECTIVES AND BRIEF SUMMARY OF THE INVENTION

It is an objective of the present invention to provide method of preparation and photosensitizer formulations based on calcium phosphate nanoparticles including stabilizers for their use in PDT, especially photodynamic tumor therapy.

It is another objective of the present invention to provide method of preparation and photosensitizer formulations based on calcium phosphate nanoparticles including stabilizers for their use in antibacterial PDT.

It is yet another object of the present invention to provide method of preparation and photosensitizer formulations of hydrophilic photosensitizers based on calcium phosphate nanoparticles without stabilizers for use in PDT.

It is yet another objective of the present invention to provide method of preparation and photosensitizer formulations based on calcium phosphate nanoparticles for their use in diagnosis, locating cells, tissues or bacteria by using fluorescence imaging methods.

Briefly stated, the present invention provides pharmaceutical photosensitizer-loaded nanoparticle formulations and their methods of preparation for photodynamic therapy, comprising a hydrophobic or hydrophilic photosensitizer, nanoparticulate calcium phosphate and in certain cases auxiliary reagents such as stabilizers. The calcium phosphate-based nanoparticle formulations of the present invention provide excellent storage stability and therapeutically effective amounts of photosensitizer for intravenous or topical administration. In a preferred embodiment, tetrapyrrole derivatives such as porphyrins, chlorins and bacteriochlorins, are the preferred hydrophobic photosensitizers to be formulated in calcium phosphate nanoparticle formulations for photodynamic tumor therapy. Additionally, 5,10,15,20-tetrakis(4-phosphonooxyphenyl)porphine (pTPPP) is a preferred hydrophilic photosensitizer for photodynamic tumor therapy. In another preferred embodiment, hydrophilic cationic and anionic photosensitizers, especially those of the phenazinium, phenothiazinium and xanthenes series have been found to inactivate pathogenic bacteria and are the preferred photosensitizers to be formulated in calcium phosphate nanoparticle formulations for antibacterial photodynamic therapy. In another embodiment, photosensitizing nanoparticle formulations are useful to locate cells, tissues or bacteria by using fluorescence imaging methods.

The objectives outlined above and other objectives, features and advantages of the present invention will become apparent from the following description read in conjunction with the accompanying figures.

BRIEF DESCRIPTION OF THE DRAWINGS

FIG. 1a-2 presents a comparison of the thermogravimetric analysis of PSS-functionalized calcium phosphate particles with and without adsorbed mTHPP.

FIG. 1a-3 displays X-ray powder diffractograms of PSS-stabilized calcium phosphate nanoparticles with and without mTHPP and vertical lines showing the calculated reflexes for hydroxyapatite.

FIG. 1a-4 shows a SEM image of PSS-functionalized and mTHPP-loaded calcium phosphate nanoparticles after ultracentrifugation.

FIG. 1a-5 presents fluorescence spectra of the mTHPP-loaded and PSS-stabilized calcium phosphate nanoparticles.

FIG. 1a-6 shows a SEM micrograph of mTHPP-loaded and PSS/PAH-functionalized calcium phosphate nanoparticles after ultracentrifugation.

FIG. 1b-1 shows UV spectra of CMC-functionalized and mTHPP loaded calcium phosphate nanoparticles.

FIG. 1b-2 presents thermogravimetric analyses of CMC-functionalized calcium phosphate particles with and without adsorbed mTHPP.

FIG. 1b-3 displays X-ray powder diffractograms of CMC-stabilized calcium phosphate nanoparticles with and without mTHPP and of calculated reflexes for hydroxyapatite.

FIG. 1b-4 shows a SEM image of the CMC-functionalized and mTHPP-loaded calcium phosphate nanoparticles.

FIG. 2-1 presents a UV spectrum of PSS-functionalized and MB-loaded calcium phosphate nanoparticles.

FIG. 2-2 shows a SEM image of the PSS-functionalized and MB-loaded calcium phosphate nanoparticles.

FIG. 3-1 shows a SEM picture of pTPPP-functionalized calcium phosphate nanoparticles after re-dispersion.

FIG. 3-2 compares the fluorescence emission spectra of dispersed pTPPP-functionalized calcium phosphate nanoparticles (effective concentration of p-TPPP: 10±2 µM) and of an aqueous solution of pTPPP (10 µM) at pH 7.4.

FIG. 3-3 shows the fluorescence emission spectrum of centrifuged (solid) pTPPP-functionalized calcium phosphate nanoparticles.

FIG. 4 shows representative results of the cell test of PSS-functionalized and mTHPP-loaded calcium phosphate nanoparticles with a concentration of mTHPP on the particles of 16.7 μM.

FIG. 5 shows the photodynamic inactivation of bacterial suspensions of Staphylococcus aureus DSM1104 (ATCC 25923) in PBS (phosphate buffered saline) by a methylene blue formulation based on calcium phosphate nanoparticles (30 minutes incubation before illumination).

FIG. 6 shows the photodynamic inactivation of bacterial suspensions of Staphylococcus aureus DSM1104 (ATCC 25923) and Pseudomonas aeruginosa DSM1117 (ATCC 27853) in PBS (phosphate buffered saline) by an mTHPP formulation based on calcium phosphate nanoparticles (90 minutes incubation before illumination).

DETAILED DESCRIPTION OF THE PREFERRED EMBODIMENTS

Figures 1, 1A:
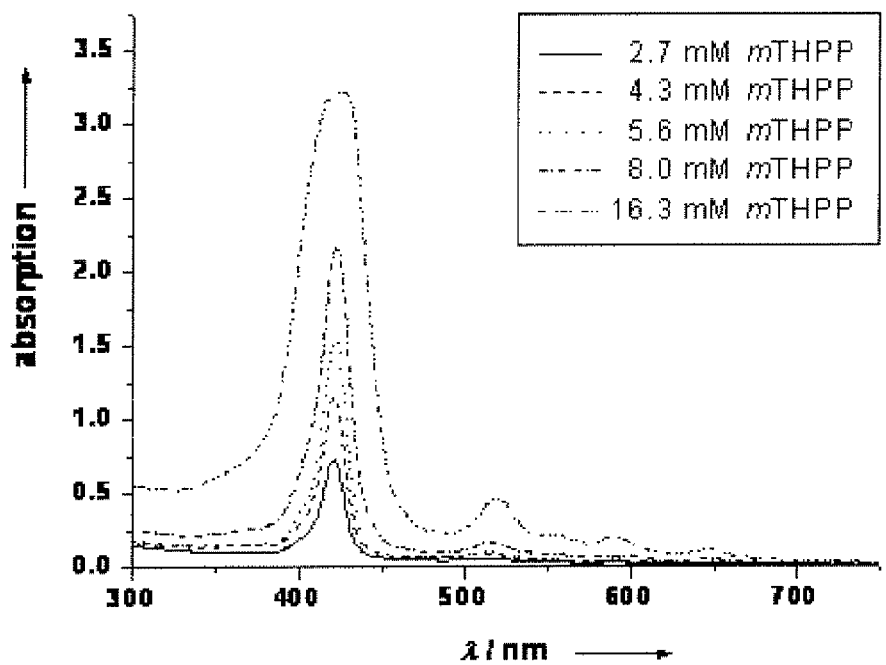
FIG. 1a-1 shows a UV spectra of PSS-functionalized and mTHPP-loaded calcium phosphate nanoparticles.

Photodynamic therapy has shown to be effective over prior art techniques in many applications such as tumor treatments and antibacterial therapies. Nevertheless, PDT efficacy depends on both the light and the photosensitizer used. Prior art photosensitizer formulations present many disadvantages such as inappropriate solubility in physiological solutions, inappropriate stability storage, long-term tissue retention, extended skin photo-toxicity and ineffectiveness in targeting unhealthy areas. Thus, there is a bigger demand for new photosensitizer formulations with better technical and physicochemical properties than prior art compounds. Present invention fulfills the needs of prior art formulations by providing a stable, easy to manufacture and handle photosensitizer formulation. Moreover, the present invention provides photosensitizer formulations with improved solubility in physiological solutions and efficient for treating hyperplasia and related diseases as well as bacterial infections. Additionally, offers novel alternatives for delivering both hydrophobic and hydrophilic photosensitizers in form of stabilized inorganic nanoparticles.

In a preferred embodiment, pharmaceutical photosensitizer-loaded nanoparticle formulations for PDT applications based on calcium phosphate are provided. They comprise a hydrophobic or hydrophilic photosensitizer, calcium phosphate and a stabilizing agent.

For tumor photodynamic treatments, hydrophilic photosensitizer is preferably but not limited to 5,10,15,20-tetrakis (4-phosphonooxyphenyl)porphine (pTPPP), whereas hydrophobic photosensitizers are preferably but not limited to tetrapyrrole-based photosensitizers, selected from porphyrins, chlorins or bacteriochlorins that have light absorption maxima in the range of 640-780 nm.

For antibacterial photodynamic therapies, the photosensitizer is preferably selected from phenazinium, phenothiazinium or xanthene dyes (namely, toluidine blue, methylene blue and their derivatives, safranin and its derivatives, erythrosine and its derivatives).

Preferred stabilizers are the anionic polyelectrolytes sodium polystyrene sulfonate (PSS) and carboxymethyl cellulose (CMC), and the cationic polyelectrolytes poly(allylamine) hydrochloride (PAH) and polyethylene imine (PEI).

It was shown that calcium phosphate nanoparticles can be stabilized by these polyelectrolytes (H. Urch, C. Geismann, M. Ulbricht, M. Epple. Materialwiss. and Werkstofftech., 2006, 37, 422-425). Furthermore, it is possible to add up to three polymer layers of alternating charge on the calcium phosphate nanoparticles using by the well-known layer-by-layer technique (G. Decher, Science, 1997, 277, 1232-1237). By suitable processes, the calcium phosphate core can be dissolved, leaving behind a polyelectrolyte capsule (J. Schwiertz, W. Meyer-Zaika, L. Ruiz-Gonzalez, J. M. Gonzalez-Calbet, M. Vallet-Regi, M. Epple, 2008, J. Mater. Chem., 18, 3831-3834). The possibility of incorporating low molecular weight species into such polymer layers deposited on polystyrene cores is known in the literature (Z. Dai, A. Voigt, S. Leporatti, E. Donath, L. Dähne, H. Möhwald, Adv. Mater. 2001, 13, 1339-1342).

In a preferred embodiment, a method of preparation of calcium phosphate-based nanoparticle photosensitizer formulations is provided. The method includes the steps of:
1) forming nanoparticles by a continuous precipitation process of calcium and phosphate solutions;
2) adding a stabilizing agent, such as PSS or CMC, during the precipitation the calcium phosphate nanoparticles;
3) adding the photosensitizer before, during or after precipitation;
4) functionalizing stabilized photosensitizer-loaded calcium phosphate particles using the layer-by-layer method.

In the case of PSS-stabilized calcium phosphate nanoparticles the photosensitizer is added to the dispersion short after precipitation. In the case of the CMC-stabilized calcium phosphate nanoparticles the photosensitizer is added to the phosphate component before the precipitation. In addition the PSS-stabilized and with photosensitizer-loaded calcium phosphate particles can be further functionalized by PAH using the layer-by-layer method. The CMC-functionalized and with photosensitizer-loaded particles can be further functionalized by PEI. Thus, there is a wide range of functionalization possibilities for the nanoparticle dispersions which also involves a strict control over their charge (anionic or cationic).

In another preferred embodiment, a method of preparation of calcium phosphate-based nanoparticle photosensitizer formulations with no need of adding a stabilizing agent is provided. The method includes the steps of:
1) forming nanoparticles by a continuous precipitation process of calcium and phosphate solutions;
2) adding the photosensitizer before, during or after precipitation.

In the case of non-functionalized calcium phosphate particles the photosensitizer is directly added to the calcium phosphate dispersion.

It is a specific advantage of the formulations of the present invention that sometimes the photosensitizer can be formulated with the calcium phosphate without using an additional stabilizing agent (Example 3). Thus, the methods described in the present invention allow the formulation of highly hydrophilic photosensitizers such as pTPPP. In general, such highly hydrophilic photosensitizers are unsuitable for photodynamic tumor therapy because of their poor water solubility. Surprisingly, it was found that a highly hydrophilic photosensitizer such as pTPPP when formulated in calcium phosphate nanoparticles as described in the present invention becomes PDT-active against HT29 tumor cells (Example 6, showing the different activity of pure pTPPP and pTPPP in a calcium phosphate nanoparticle formulation).

Photosensitizing nanoparticle formulations are useful to target the photosensitizer molecule to the unwanted cells or tissues or bacterial cells or other undesirable objects and, after irradiation with an appropriated light source, to damage the target. Additionally, in another embodiment the photosensitizing formulations are also useful to locate unwanted cells or tissues or bacterial cells or other undesirable objects by using fluorescence imaging methods with generally ultraviolet absorbed wavelengths to generate visible fluorescence (compare Example 3). The imaging can be done without or in conjunction with photochemical activation of the photosensitizer, by irradiations generally of visible or near-infrared wavelengths.

Calcium phosphate constitutes the inorganic mineral of mammalian bone and teeth and therefore the calcium phosphate nanoparticles are well tolerated by the body. Thus, they function as very efficient transporters for drug substances with a high biocompatibility and biodegradability. By binding the photosensitizer onto and into the calcium phosphate nanoparticles, water insoluble photosensitizers can dispersed in water. Thereby, the application of alcoholic solutions can be avoided.

The following examples are presented to provide those of ordinary skill in the art with a full and illustrative disclosure and description of how to make the photosensitizer-loaded calcium phosphate nanoparticles of the invention and show their photodynamic activity and are not intended to limit the scope of what the inventor regards as the invention. All efforts were made to ensure accuracy with respect to numbers used (e.g. amounts, temperature etc.), but some experimental errors and deviations should be accounted for.

Example 1a

Description of the Preparation of a Formulation Comprising PSS-Stabilized Calcium Phosphate Nanoparticles and a Hydrophobic Photosensitizer, 5,10,15,20-tetrakis(3-hydroxyphenyl)-porphyrin (mTHPP)

The PSS-coated nanoparticles were prepared at room temperature by rapidly pumping aqueous solutions of calcium lactate (18 mM), $(NH_4)_2HPO_4$ (10.8 mM), and PSS (2 g $l^{-1}$) in a volume ratio of 1:1:2 into a stiffed vessel containing 4 volume parts of water. The PSS functionalized and stabilized the emerging calcium phosphate nanoparticles (H. Urch, C. Geismann, M. Ulbricht, M. Epple, Materialwiss. and Werkstofftech., 2006, 37, 422-425.). The pH of the calcium and phosphate solutions was previously adjusted to 10 with ammonia solution. After one minute, mTHPP (1.5 mM in 2-propanol) was added in a volume ratio of 1:5 up to 1:1 with respect to the volume of the phosphate solution. The final pH of the colloidal dispersion was 9.3 to 9.5. After 4 days the particles were separated from the counter ions (lactate, $NH_4^+$, $Na^+$), an excess of PSS (dissolved) and non-adsorbed mTHPP by ultracentrifugation at 66,000 g for 30 minutes. The centrifuged nanoparticles were redispersed in water, centrifuged and redispersed again. Ultrapure water (Purelab ultra instrument from ELGA) was used for all preparations.

The products were characterized by various analytical methods. Thermogravimetric analysis (TG) was carried out with a Netzsch STA 409 PC instrument (dynamic oxygen atmosphere 50 ml $min^{-1}$; heating rate 1 K $min^{-1}$; open alumina crucible). X-ray powder diffraction (XRD; Siemens D500 diffractometer; Cu Kα radiation, λ=1.54 Å), and scanning electron microscopy coupled with energy-dispersive X-ray spectroscopy (SEM-EDX; ESEM Quanta 400 FEG, FEI; gold-palladium [80:20]-sputtered samples; EDX detector: S-UTW-Si(Li)). Dynamic light scattering (DLS) and zeta potential determinations were performed with a Zetasizer nanoseries (Malvern Nano-ZS, laser: λ=532 nm) instrument. Emission and excitation spectra were measured at room temperature using a J&M spectrofluorometer (Analytische Mess- and Regeltechnik FL3095-500) equipped with a diode array polychromator and a 75 W xenon lamp. The emission spectra were corrected for the detector sensitivity and the excitation spectra for the intensity of the exciting light. UV-visible absorption spectra were recorded with a Varian Cary WinUV spectrophotometer in 1 cm quartz cuvettes.

The amount of mTHPP absorbed on the particles was determined by UV-spectroscopy by recording a calibration curve. FIG. 1a-1 shows the typical absorption spectrum of the mTHPP-loaded calcium phosphate colloid. This absorption spectrum is similar to the absorption spectrum of dissolved mTHPP.

Figures 1, 1A, 2:
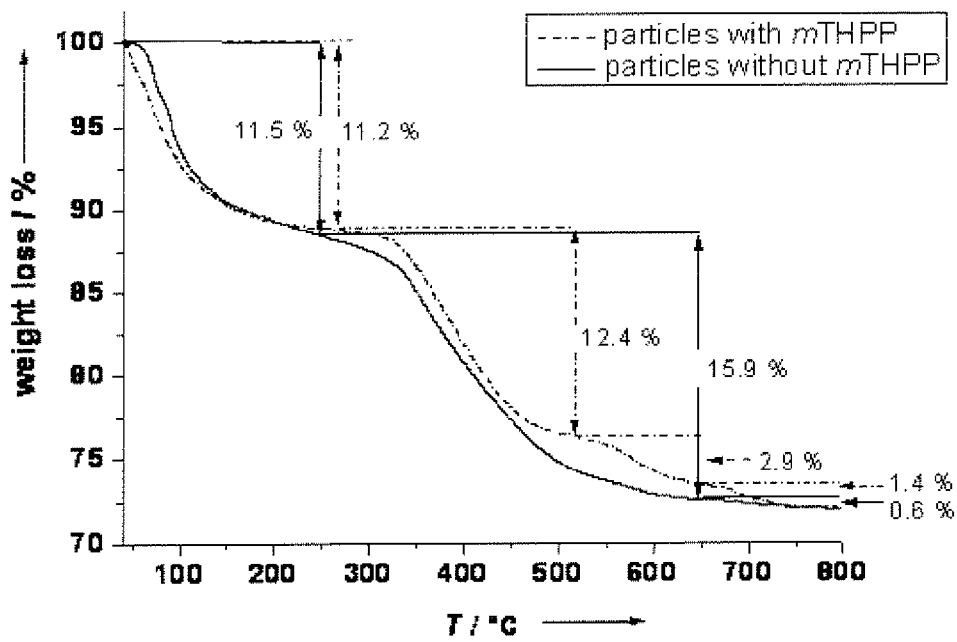

FIG. 1a-2 shows the thermogravimetric analysis of the PSS-functionalized calcium phosphate nanoparticles with and without adsorbed mTHPP. The first weight loss corresponds to the water loss of the compounds which is very similar for both sample types. The second weight loss shows the combustion of the polymeric part; in this case the amount of polymer differs by about 3.5%. Apparently the mTHPP inhibits the PSS-adsorption to some extent. The third weight loss of 2.9% of the mTHPP-loaded calcium phosphate nanoparticles corresponds to the combustion of mTHPP which is missing for the non-loaded particles. This amount of mTHPP is in agreement with the results from quantitative UV spectroscopy. The last weight loss shows the loss of carbon dioxide due to the carbonate content of the mineral phase. These results were also confirmed by elemental analysis (C, H, N, Ca, $PO_4^{3-}$). The calcium to phosphate ratio is 1.67, i.e. the ratio of stoichiometric hydroxyapatite.

FIG. 1a-3 shows the X-ray powder diffractograms of PSS-stabilized calcium phosphate nanoparticles with and without adsorbed mTHPP. The particles consist of nanocrystalline hydroxyapatite, $Ca_5(PO_4)_3(OH)$, as indicated by the broad diffraction peaks.

FIG. 1a-4 shows a SEM-image of PSS-functionalized and mTHPP-loaded calcium phosphate nanoparticles. The particles are approximately 80-100 nm in diameter with a rather monodisperse size distribution.

Dynamic light scattering measurements confirmed these results. The zeta potential of the particles is approximately −20 mV. Despite the comparatively low zeta potential the particles are stable in dispersion for several weeks.

In addition it was possible to deposit another polymeric layer on the PSS-functionalized and mTHPP-loaded calcium phosphate particles by the layer-by-layer technique (G. Decher, Science, 1997, 277, 1232-1237; J. Schwiertz, W. Meyer-Zaika, L. Ruiz-Gonzalez, J. M. Gonzalez-Calbet, M. Vallet-Regi, M. Epple, J. Mater. Chem., 2008, 18, 3831-3834). PAH, a cationic polyelectrolyte, (4 g $l^{-1}$, pH 7) was added to the particle dispersion in a 1:1 volume ratio. The particles were separated from the excess of PAH by ultracentrifugation at 66,000 g for 30 minutes. The centrifuged nanoparticles were redispersed in ultrapure water. The UV-spectra were similar to the ones without a second polymeric layer. Fluorescence measurements show a decrease in fluorescence intensity with the deposition of the PAH-layer (FIG. 1a-5).

Dynamic light scattering measurements showed a slight increase of particle diameter. This was confirmed by SEM (FIG. 1a-6). The diameter of the particles is 100-120 nm. The zeta potential is approximately +50 mV which confirms the adsorption of the cationic polyelectrolyte PAH.

Example 1b

Description of the Preparation of a Formulation Comprising CMC-Stabilized Calcium Phosphate Nanoparticles and a Hydrophobic Photosensitizer, 5,10,15,20-tetrakis(3-hydroxyphenyl)-porphyrin (mTHPP)

The CMC-coated calcium phosphate nanoparticles were prepared at room temperature by rapidly pumping aqueous solutions of calcium lactate (18 mM), (NH$_4$)2HPO$_4$ (10.8 mM), and CMC (2 g l$^{-1}$) in a volume ratio of 1:1:1 into a stirred vessel containing 4 volume parts of water. Before the precipitation the photosensitizer mTHPP (1.5 mM in 2-propanol) was mixed to the phosphate component in a volume ratio of 20:1 up to 5:1 with respect to the volume of phosphate solution. The CMC functionalized and stabilized the emerging calcium phosphate nanoparticles. The pH of the calcium and phosphate solutions was previously adjusted to 10 with ammonia solution. The final pH of the colloidal dispersion was 9.2 to 9.5. The particles were separated from the counter ions (lactate, NH$_4^+$, Na$^+$), excess of dissolved CMC and non-adsorbed mTHPP by ultracentrifugation at 66,000 g for 30 minutes. The centrifuged nanoparticles were redispersed in water, centrifuged and redispersed again. Ultrapure water (Purelab ultra instrument from ELGA) was used for all preparations. To accomplish the stability of this colloidal system, the dispersion had to be diluted in the volume ratio 1:5 with water.

The products were characterized by various analytical methods. Thermogravimetric analysis (TG) was carried out with a Netzsch STA 409 PC instrument (dynamic oxygen atmosphere 50 ml min$^{-1}$; heating rate 1 K min$^{-1}$; open alumina crucible). X-ray powder diffraction (XRD; Siemens D500 diffractometer; Cu Kα radiation, λ=1.54 Å), and scanning electron microscopy coupled with energy-dispersive X-ray spectroscopy (SEM-EDX; ESEM Quanta 400 FEG, FEI; gold-palladium [80:20]-sputtered samples; EDX detector: S-UTW-Si(Li)). Dynamic light scattering (DLS) and zeta potential determinations were performed with a Zetasizer nanoseries (Malvern Nano-ZS, laser: λ=532 nm) instrument. Emission and excitation spectra were measured at room temperature using a J&M spectrofluorometer (Analytische Mess- and Regeltechnik FL3095-500) equipped with a diode array polychromator and a 75 W xenon lamp. The emission spectra were corrected for the detector sensitivity and the excitation spectra for the intensity of the exciting light. UV-visible absorption spectra were recorded with a Varian Cary WinUV spectrophotometer in 1 cm quartz cuvettes.

The amount of mTHPP absorbed on the particles was measured by UV-spectroscopy. FIG. 1b-1 shows the typical absorption of the mTHPP-loaded calcium phosphate colloid. Except for broader peaks, the absorption spectrum is close to the absorption spectrum. of free mTHPP.

FIG. 1b-2 shows the results of the thermogravimetric analysis of the CMC-functionalized calcium phosphate nanoparticles with and without adsorbed mTHPP. The first weight loss corresponds to the water loss of the compounds. This is 4.5% higher for the mTHPP-loaded particles than for the unloaded particles. The second weight loss is due to the combustion of the polymer; in this case the amounts differ by 3.3%. Apparently in this case, the mTHPP promotes the CMC-adsorption to some extent. The third weight loss of 2.6% of the mTHPP-loaded calcium phosphate nanoparticles is due to the combustion of mTHPP. The last weight loss shows the loss of carbon dioxide due to the carbonate content of the mineral phase. These results are confirmed by elemental analysis. The calcium to phosphate ratio is 1.76 which is a bit higher than the ratio of stoichiometric hydroxyapatite (1.67).

FIG. 1b-3 shows the X-ray powder diffractograms of CMC-stabilized calcium phosphate nanoparticles with and without adsorbed mTHPP. The particles are X-ray amorphous, i.e. no defined peaks are recognizable. The vertical lines show the calculated peak positions for hydroxyapatite, Ca$_5$(PO$_4$)$_3$(OH).

FIG. 1b-4 shows an SEM image of CMC-functionalized and mTHPP-loaded calcium phosphate nanoparticles. The particles are approximately 80-100 nm in diameter with a rather monodisperse size distribution.

Dynamic light scattering measurements confirmed these results. The zeta potential of the particles is approximately −20 mV. Despite the low zeta potential the particles are stable in dispersion for several weeks.

In addition it was possible to deposit another polymeric layer on the CMC-functionalized and mTHPP-loaded calcium phosphate particles by the layer-by-layer technique (G. Decher, Science, 1997, 277, 1232-1237; J. Schwiertz, W. Meyer-Zaika, L. Ruiz-Gonzalez, J. M. Gonzalez-Calbet, M. Vallet-Regi, M. Epple, J. Mater. Chem., 2008, 18, 3831-3834). The cationic polyelectrolyte PEI (2 g l$^{-1}$, pH 10.4) was added to the particle dispersion in a 8:1 volume ratio. The particles were separated from the excess of PEI by ultracentrifugation at 66,000 g for 30 minutes. The centrifuged nanoparticles were redispersed in ultrapure water. The size of the particles increased to about 40 nm and the zeta potential was +30 mV which confirms the adsorption of the positive polyelectrolyte PEI. The particles are stable in dispersion for a few weeks.

In conclusion it was possible to prepare different functionalized calcium phosphate nanoparticles loaded with mTHPP. All colloidal systems were stable for several weeks. The size distributions of all samples were below a polydispersity index (PDI) of 0.3 which illustrates the reliability of the dynamic light scattering measurements. SEM images confirm a narrow size distribution. The quantity of adsorbed mTHPP on the calcium phosphate nanoparticles was measured by UV-spectroscopy and thermogravimetric analysis. The internal structure of the particles ranges from amorphous to nanocrystalline hydroxyapatite.

Example 2

Description of the Preparation of a Formulation Comprising Calcium Phosphate Nanoparticles and the Hydrophilic Photosensitizer Methylene Blue (MB)

The PSS-coated nanoparticles were prepared at room temperature by rapidly pumping aqueous solutions of calcium lactate (18 mM), (NH$_4$)$_2$HPO$_4$ (10.8 mM), and PSS (2 g l$^{-1}$) in a volume ratio of 1:1:2 into a stirred vessel containing 4 volume parts of water. The PSS functionalized and stabilized the forming calcium phosphate nanoparticles. The pH of the calcium and phosphate solutions was previously adjusted to 10 with potassium hydroxide solution. After one minute MB (0.003 M) was added in a volume ratio of 1:1 with respect to the phosphate solution. The particles were separated from the counter ions (lactate, NH$_4^+$, K$^+$, Na$^+$, Cl$^-$), excess of dissolved PSS and non-adsorbed MB by ultracentrifugation at 150,000 g for 30 minutes. The centrifuged nanoparticles were redispersed in water, centrifuged and redispersed again. Ultrapure water (Purelab ultra instrument from ELGA) was used for all preparations.

The products were characterized by various analytical methods. Thermogravimetric analysis (TG) was carried out with a Netzsch STA 409 PC instrument (dynamic oxygen atmosphere 50 ml min$^{-1}$; heating rate 1 K min$^{-1}$; open alumina crucible). X-ray powder diffraction (XRD; Siemens D500 diffractometer; Cu Kα radiation, λ=1.54 Å), and scanning electron microscopy coupled with energy-dispersive X-ray spectroscopy (SEM-EDX; ESEM Quanta 400 FEG, FEI; gold-palladium [80:20]-sputtered samples; EDX detector: S-UTW-Si(Li)). Dynamic light scattering (DLS) and zeta potential determinations were performed with a Zetasizer nanoseries (Malvern Nano-ZS, laser: λ=532 nm) instrument. Emission and excitation spectra were measured at room temperature using a J&M spectrofluorometer (Analytische Mess- and Regeltechnik FL3095-500) equipped with a diode array polychromator and a 75 W xenon lamp. The emission spectra were corrected for the detector sensitivity and the excitation spectra for the intensity of the exciting light. UV-visible absorption spectra were recorded with a Varian Cary WinUV spectrophotometer in 1 cm quartz cuvettes.

The amount of MB absorbed on the particles was measured by UV-spectroscopy. FIG. 2-1 shows the typical absorption of the MB loaded calcium phosphate colloid. This absorption pattern is similar to the absorption pattern of the free MB.

FIG. 2-2 shows a SEM image of PSS-functionalized and MB-loaded calcium phosphate nanoparticles. The particles are approximately 50-80 nm in diameter with a rather monodisperse size distribution. The zeta potential of these particles is approximately −20 mV. Despite the comparatively low zeta potential the particles are stable in dispersion for several weeks.

In conclusion it was possible to prepare PSS-functionalized calcium phosphate nanoparticles loaded with MB. These particles were stable for several weeks. The size distribution of the sample was below a polydispersity index of 0.3 which illustrates the reliability of the dynamic light scattering measurements. SEM images confirm the narrow size distribution. The quantity of adsorbed MB on the calcium phosphate nanoparticles was confirmed by UV-spectroscopy.

Example 3

Description of the Preparation of a Formulation Comprising Calcium Phosphate Nanoparticles and a Hydrophilic Phosphate-Functionalized Photosensitizer (pTPPP)

Calcium phosphate nanoparticles were prepared by pumping aqueous solutions of $Ca(NO_3)_2.4H_2O$ (3 mM) and $(NH_4)_2HPO_4$ (1.8 mM) into a stirred vessel (T. Wetzel, I. Radtke, W. Meyer-Zaika, R. Heumann and M. Epple, J. Mater. Chem., 2004, 14, 2213-221.7). The pH of the calcium and phosphate solutions was previously adjusted to 9 with 0.1 N aqueous NaOH. A few seconds after mixing, the nanoparticle dispersion was taken with a syringe. The colloids were prepared by rapidly mixing an aqueous solution of the sodium salt of pTPPP (30 μM) with the dispersed calcium phosphate nanoparticles in a 5 ml:10 ml ratio. The final pH of the colloidal dispersion was between 7.5 and 8.5. The colloids were stored at 4 to 8° C. under light exclusion. The particles were separated from the counter ions ($NO_3^-$, $NH_4^+$, $Na^+$) and non-adsorbed pTPPP by ultracentrifugation at 371,000 g. The centrifuged nanoparticles were washed with 100 ml of absolute ethanol and either redispersed in water or dried in air. Ultrapure water (Purelab ultra instrument from ELGA) was used for all preparations.

The amount of dissolved pTPPP in the supernatant after ultracentrifugation was about 30% as determined by UV spectroscopy, i.e. about 70% of the total amount of the added pTPPP was adsorbed on the calcium phosphate surface. The content of pTPPP in the nanoparticles was estimated as follows by taking the amounts of porphyrin, calcium and phosphate used in the synthesis: If we assume that all calcium and phosphate did precipitate from the solution as hydroxyapatite, i.e. $Ca_5(PO_4)_3OH$, the maximum content of pTPPP in the solid phase is about 0.7×5.5 wt %=3.9 wt %. Elemental analysis of the pTPPP-doped nanoparticles by combustion elemental analysis gave 2.32 wt % C and 2.73 wt % H. As hydrogen can also come from hydroxide groups and from adsorbed water, we used only the carbon content which gave a loading of 5.2 wt % pTPPP in the solid. We conclude that the loading of pTPPP in the solid is around 4-5 wt %. We ascribe the difference between the two methods to experimental uncertainties.

The adsorbing dye pTPPP and the functionalized nanoparticles were characterized by NMR spectroscopy (Bruker 300 MHz), ESI-MS spectrometry (Bruker BioTOF III equipped with an electrospray ionization gun), X-ray powder diffraction (XRD; Siemens D500 diffractometer; Cu Kα radiation, λ=1.54 Å), Fourier transform infrared spectroscopy (FTIR; Bruker-Vortex 70 instrument), and scanning electron microscopy coupled with energy-dispersive X-ray spectroscopy (SEM-EDX; ESEM Quanta 400 FEG, FEI; gold-palladium [80:20]-sputtered samples; EDX detector: S-UTW-Si(Li)). Dynamic light scattering (DLS) and zeta potential determinations were performed with a Zetasizer nanoseries (Malvern Nano-ZS, laser: λ=532 nm) instrument. Emission and excitation spectra were measured at room temperature using a J&M spectrofluorometer (Analytische Mess- and Regeltechnik FL3095-500) equipped with a diode array polychromator and a 75 W xenon lamp. The emission spectra were corrected for the detector sensitivity and the excitation spectra for the intensity of the exciting light. UV-visible absorption spectra were recorded with a Varian. Cary WinUV spectrophotometer in 1 cm quartz cuvettes.

Figures 1, 1A, 2, 3:
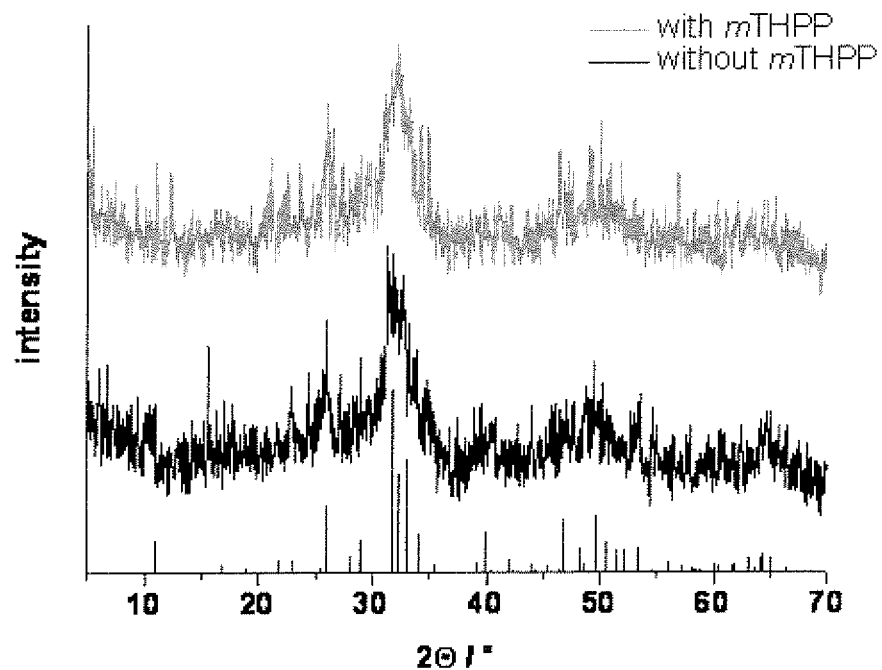
Figures 1, 1A, 2, 3, 4:
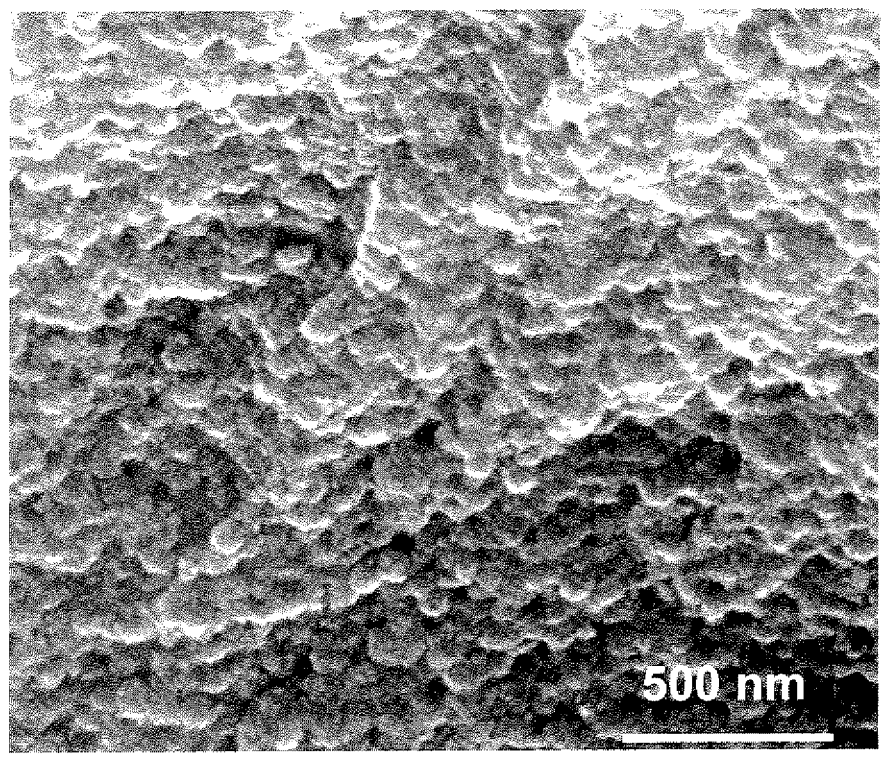

Scanning electron microscopy showed approximately spherical nanoparticles (FIG. 3-1).

At an excitation wavelength of 410 nm, the emission spectrum of the dispersed colloid consists of a strong band at 653 nm with a shoulder at 705 nm (FIG. 3-2). At pH 7.4, the partially protonated form of pTPPP shows two strong bands at 650 nm and 712 nm in the emission spectrum. This spectrum was compared with the emission spectrum of the dispersed nanoparticles. In the case of the dispersed nanoparticles, a broad shoulder was observed at 705 nm instead of a strong peak at 712 nm. The observed spectral changes in the absorption and emission spectra of the dispersed nanoparticles are probably caused by the electrostatic interaction of pTPPP with the calcium phosphate surface. The emission spectrum of the centrifuged (solvent-free, i.e. solid) pTPPP-functionalized calcium phosphate nanoparticles was also measured. The particles were excited in the near UV region at 306 nm (FIG. 3-3). The emission spectrum showed two strong peaks at 472 nm and 597 nm, in good agreement with the solid porphyrin.

As is apparent from FIGS. 3-2 and 3-3, the pTPPP-loaded nanoparticles show a fluorescence signal which can be used for their detection in vivo.

Example 4

Cell-Test of the Formulation from Example 1 (with the Photosensitizer mTHPP) on a HT29 Tumor Cell Line The cell test was conducted according to the following procedure:

The photosensitizing activity was determined in the human colon adenocarcinoma cell line HT29. The HT29 cell lines were grown in DMEM (cc-pro GmbH) supplemented with 10% heat-inactivated fetal calf serum (FCS, cc-pro GmbH), 1% penicillin (10000 IU) and streptomycin (10,000 µg ml$^{-1}$, cc-pro GmbH). Cells were kept as a monolayer culture in a humidified incubator (5% $CO_2$ in air at 37° C.).

A stock solution of the nanoparticle formulation was kept in the dark at 4° C. Further dilution was performed in RPMI 1640 medium without phenol red supplemented with 10% FCS to reach a final photosensitizer concentration of 2 or 10 µM, respectively.

$2\text{-}10^4$ cells ml$^{-1}$ were seeded in micro plates ($2\text{-}10^5$ cells per well). Cells were incubated with fresh medium (RPMI without phenol red) containing 10% FCS with 2 or 10 µM of the photosensitizer for 24 h before light exposure. Before photosensitization, cells were washed, incubated with RPMI without phenol red and 10% FCS, then irradiated at room temperature with a 652 nm diode laser (Ceralas PDT 652, biolitec AG) at a fixed fluence rate of 100 mW cm$^{-2}$ (50 J cm$^{-2}$). Following irradiation, the cells were incubated in a humidified incubator (5% $CO_2$, in air at 37° C.) for 24 h until cell viability assay.

The cell viability was assessed by the XTT assay. 500 mg XTT (sodium 3'-[phenylamino-carbonyl)-3,4-tetrazolium]-bis(4-methoxy-6-nitro)benzene sulfonic acid, Applichem GmbH) is dissolved in 500 ml PBS-Buffer (without $Ca^{2+}$ and $Mg^2$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer The solution should be stored frozen and should not be exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with fresh RPMI without phenol red and 10% FCS (100 µl) prior adding 50 µl XTT reaction solution per well. The micro plate was incubated for 2-3 hours at 37° C. and 5% $CO_2$ until an orange dye is to be formed. The micro plate was gently shaken to evenly distribute the dye in the wells.

The absorbance of the samples was measured with a spectrophotometer (Tecan Infinite 200, Tecan Group Ltd.) at a wavelength of 490 nm. In order to measure reference absorbance (to measure non-specific readings) a wavelength of 630-690 nm was used.

Example 5

Cell-Test of the Formulation from Example 2 (with the Photosensitizer MB) on a Bacterial Cell Culture The test was conducted according to the following procedure:

The bacterial strains used in our studies was the Gram-positive bacterium *Staphylococcus aureus* DSM1104 (ATCC 25923) and *Pseudomonas aeruginosa* DSM1117 (ATCC 27853). The cells of this strain were grown aerobically overnight at 37° C. in Tryptic Soy Broth (Merck KGaA Darmstadt, Germany). Cells were harvested by centrifugation and resuspended in sterile phosphate-buffered saline (PBS). The final OD (optical density) at 600 nm, 1 cm path length, was 0.015. Aliquots (190 µl) of the bacterial suspensions were placed into sterile black 96-well plates with clear bottom (Costar® 3603, Corning Inc., USA). 10 µl of a methylene blue formulation based on calcium phosphate nanoparticles were added. The plates were incubated for 30 minutes in the dark at room temperature. After incubation the samples were exposed to light from a 665 nm diode laser (Ceralas PDT, biolitec AG, Germany), power set to 0.55 W, irradiation time of 100 s via a light fiber from the bottom of the plate. The fluence rate for these Settings was about 1 W cm$^{-2}$ (measured with Optometer P-9710, Gigahertz-Optik GmbH, Puchheim, Germany). With this irradiation time, the resulting energy fluence was about 100 J cm$^{-2}$. A control well contained 10 µl of PBS instead of methylene blue formulation and was not exposed to laser light. The control sample for dark toxicity contained the methylene blue formulation but was not exposed to laser light. After illumination the samples were removed from the wells of the plate, diluted with Tryptic Soy Broth and plated by using spiral plater Eddy Jet (iul Instruments, Barcelona, Spain) on Tryptic Soy agar plates. The numbers of colony-forming units (CFU ml$^{-1}$) were enumerated after adequate incubation by using colony Counter Countermat Flash (iul Instruments, Barcelona, Spain).

Figures 1, 1A, 2, 3, 4, 5:
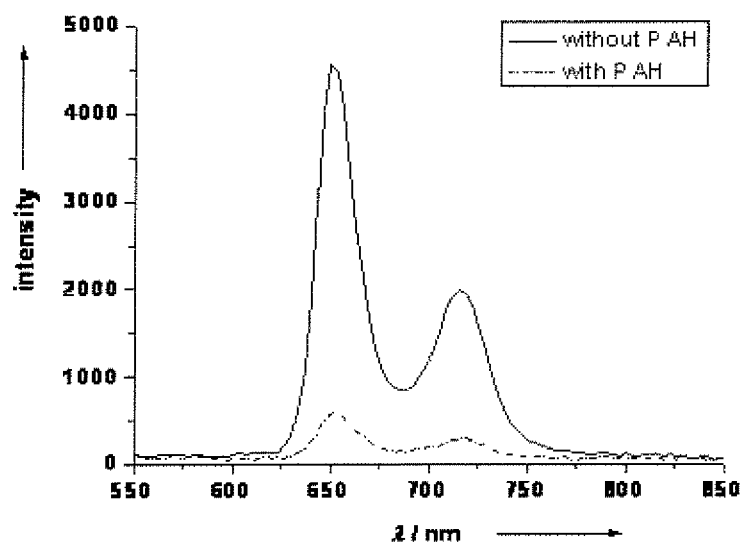

Results of this experiment are shown in FIG. 5. A killing effect of about 90% by PDT treatment was found.

Example 6

Cell Test of the Formulation from Example 1b (with the Photosensitizer mTHPP) on a Bacterial Cell Culture For this test, the CMC/PEI functionalized calcium phosphate particles were used.

The test was conducted according to the procedure given in EXAMPLE 5 except that the incubation time was 30 min and 90 min, respectively.

Figures 1, 1A, 2, 3, 4, 5, 6:
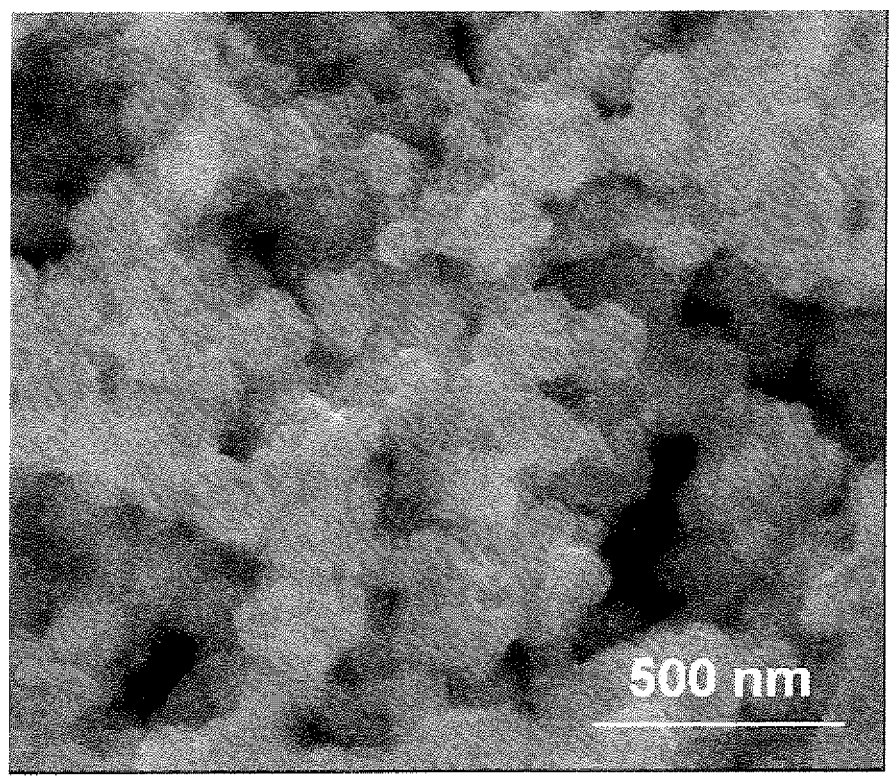
Figures 1, 1B:
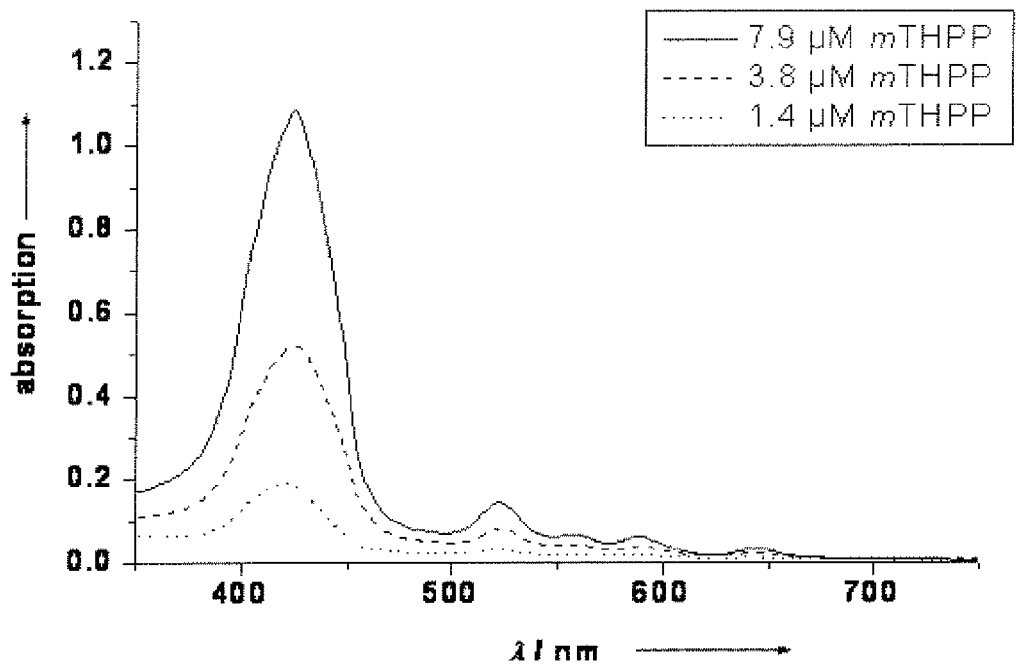
Figures 1, 1B, 2:
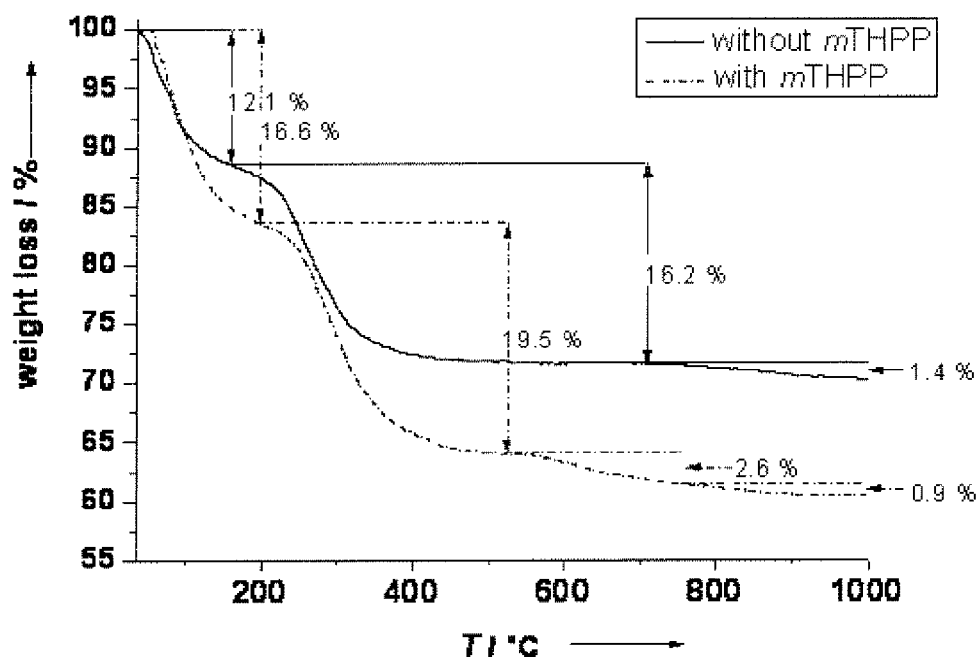
Figures 1, 1B, 2, 3:
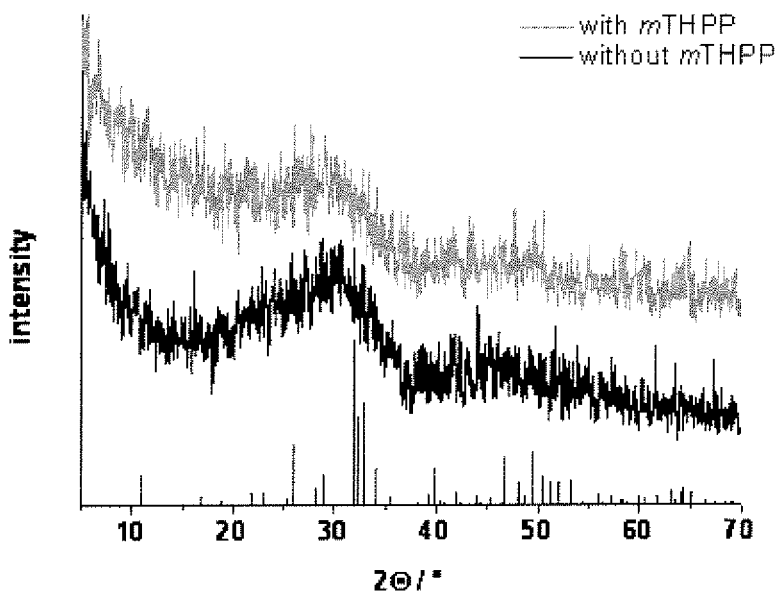
Figures 1, 1B, 2, 3, 4:
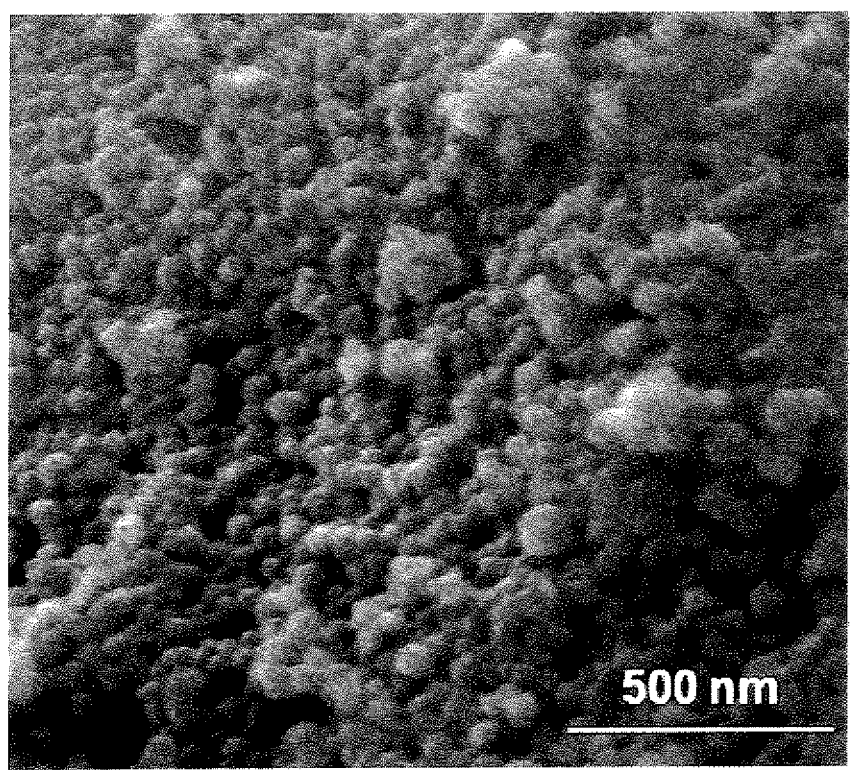
Figures 1, 2:
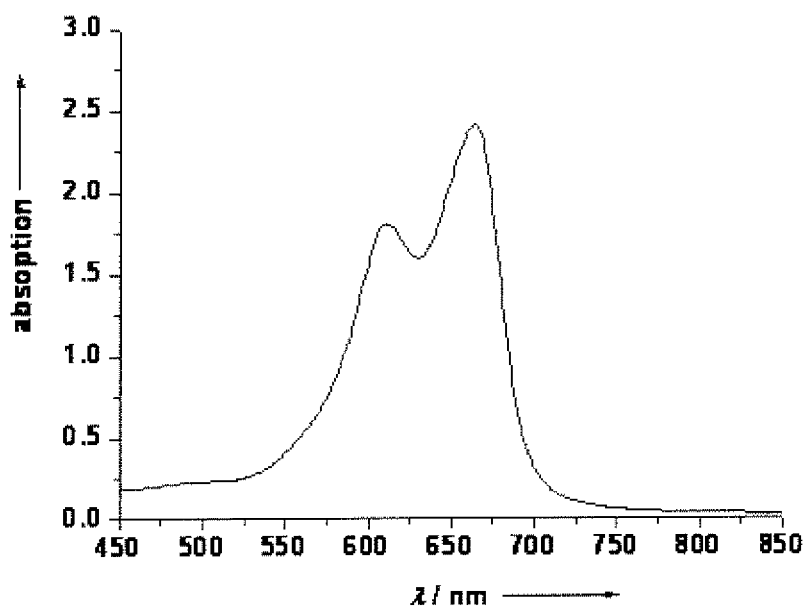
Figure 2:
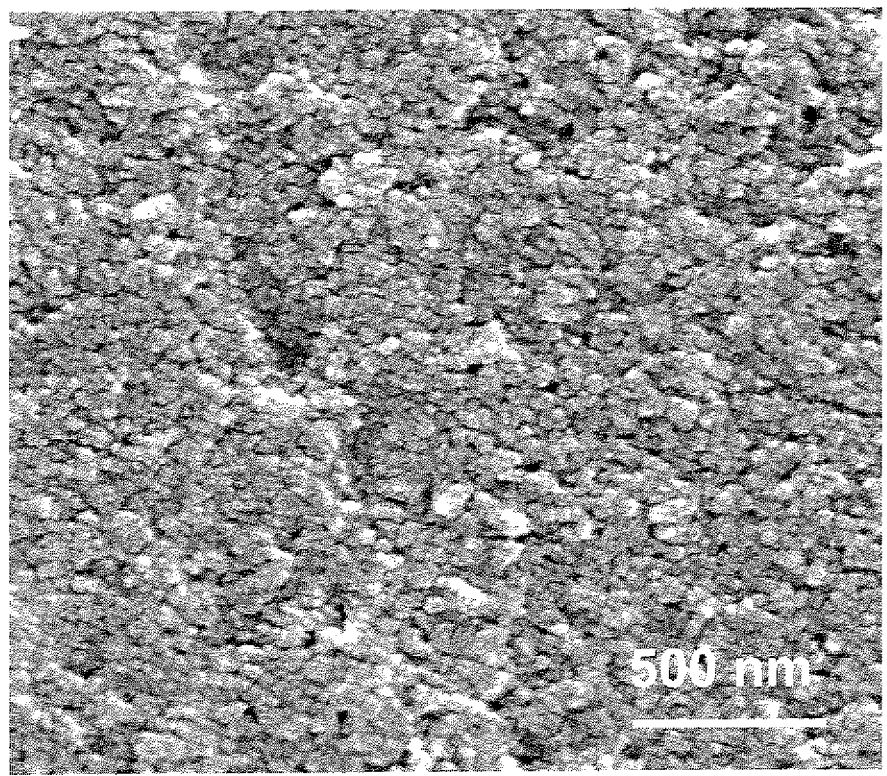
Figures 1, 3:
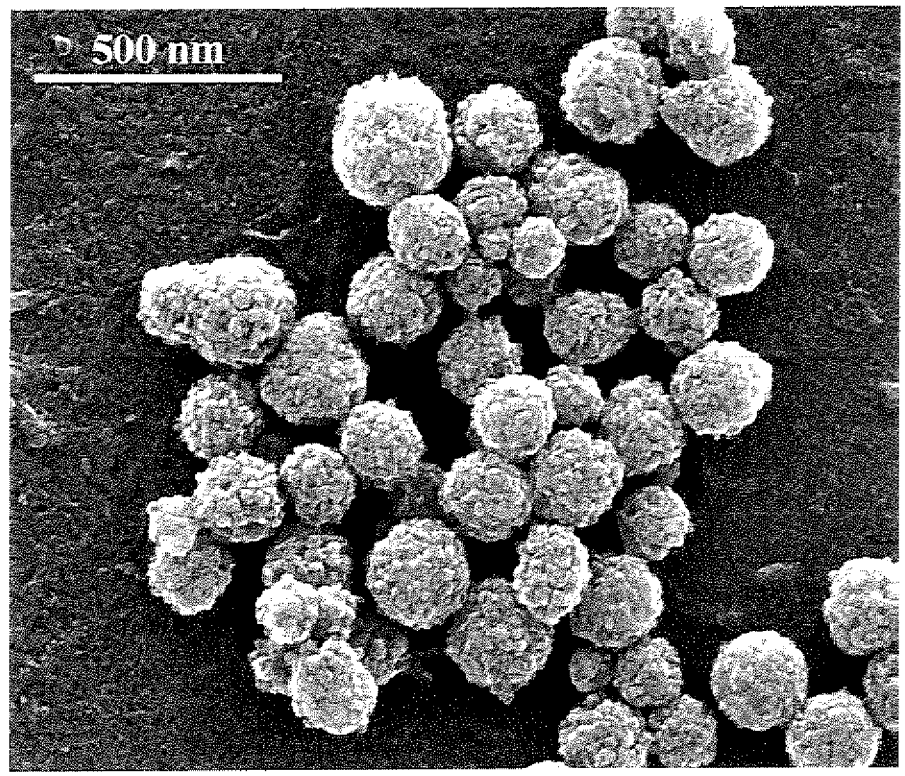
Figures 2, 3:
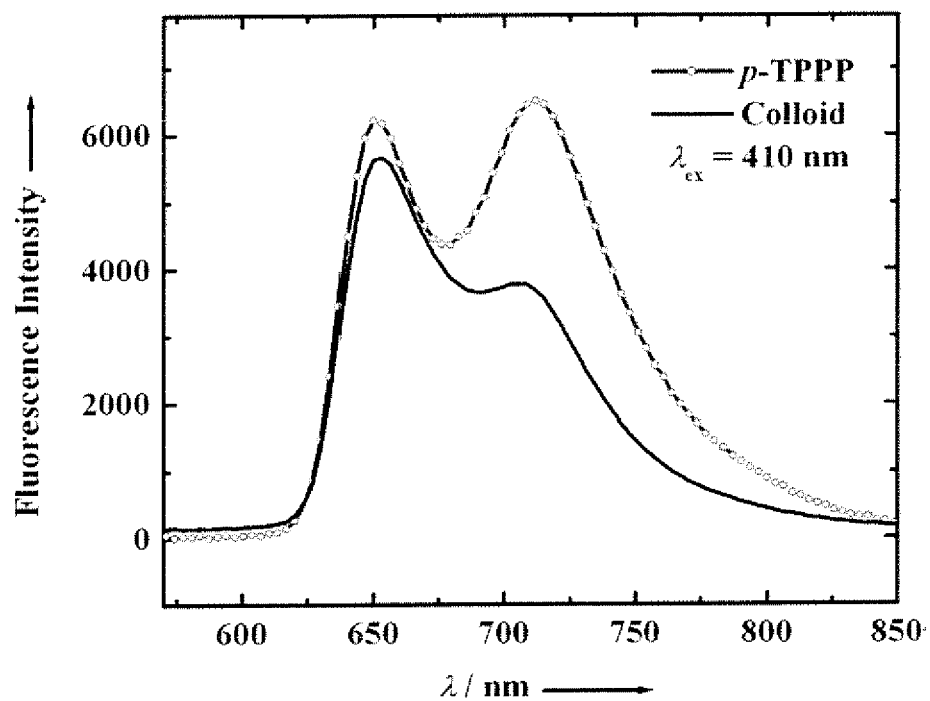
Figure 3:
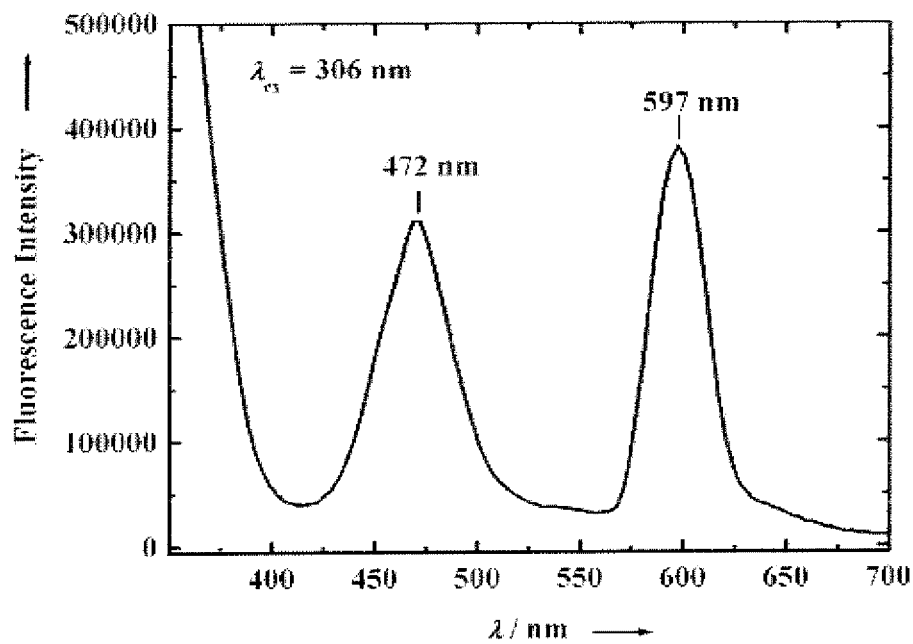
Figure 4:
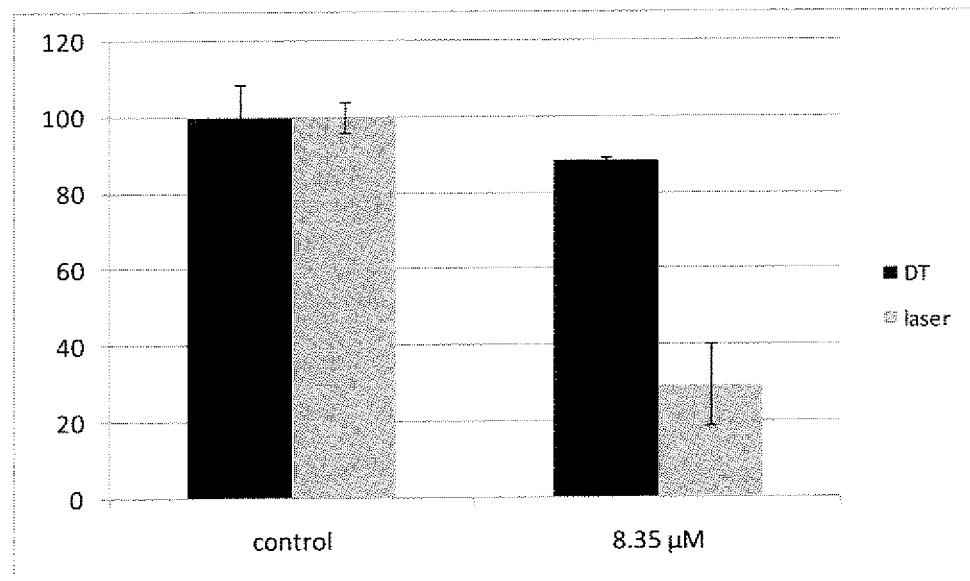
Figure 5:
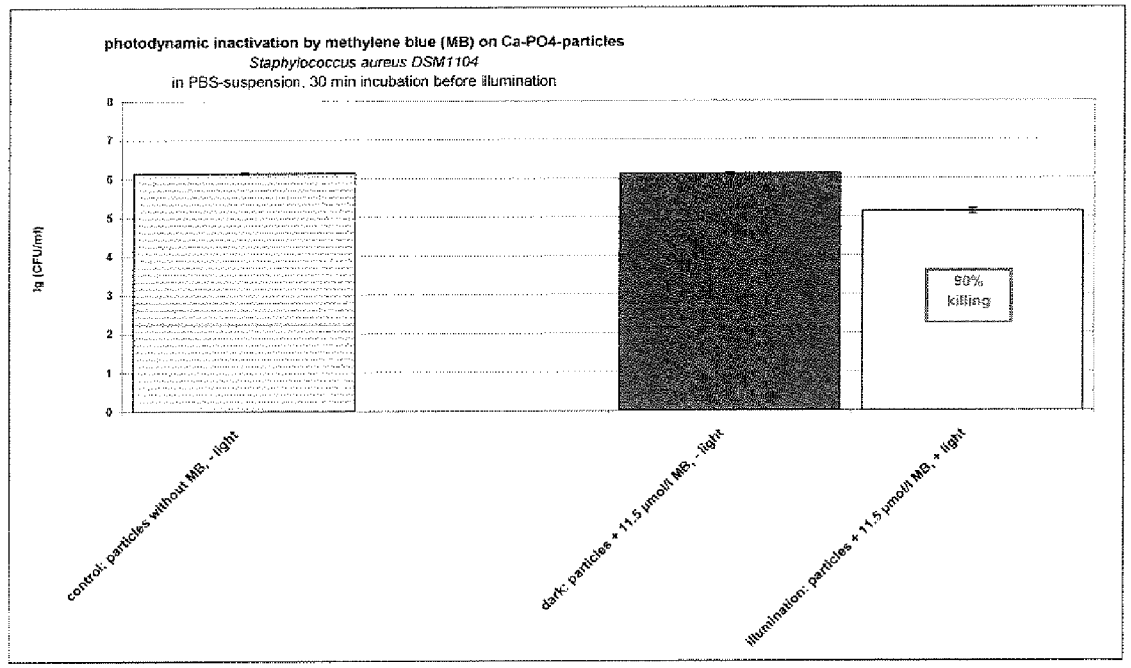
Figure 6:
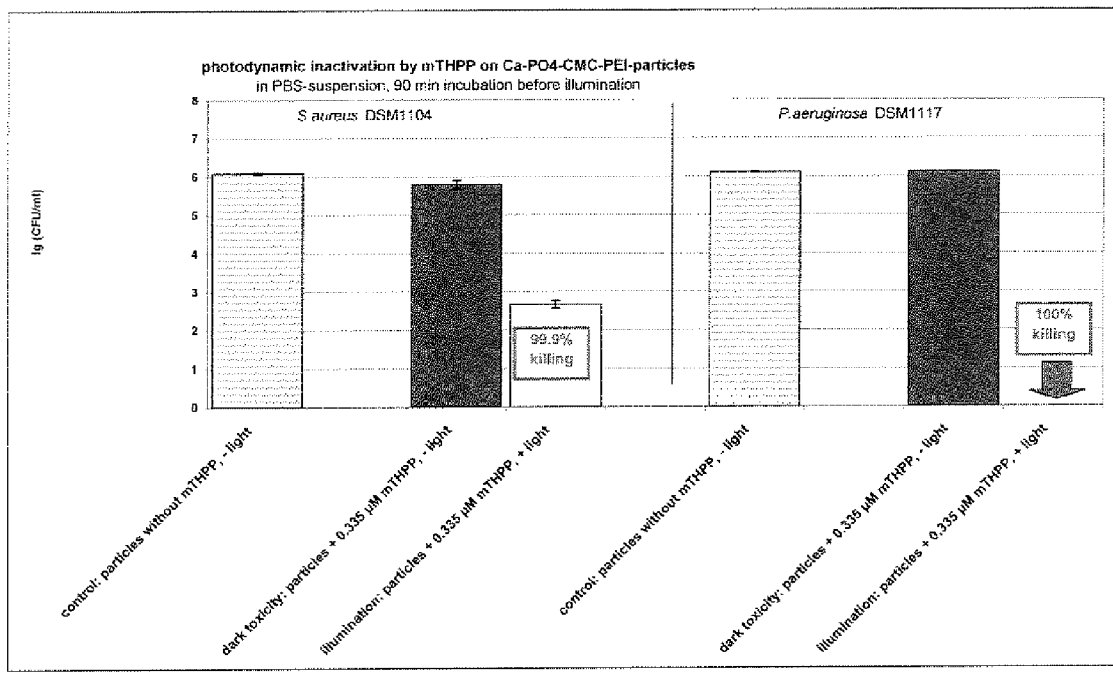

The results of this experiment are shown in FIG. 6. A killing effect of about 98 to 100% by the PDT treatment was found against both Gram-positive and Gram-negative bacterial strains.

Example 7

Cell-Test of the Formulation from Example 3 (with the Photosensitizer pTPPP) and of the Pure Photosensitizer pTPPP on a HT29 Tumor Cell Line The test was conducted according to procedure given in EXAMPLE 4. The concentration of the pure photosensitizer solution was adjusted as to equal the amount contained in the nanoparticles.

Figure 7:
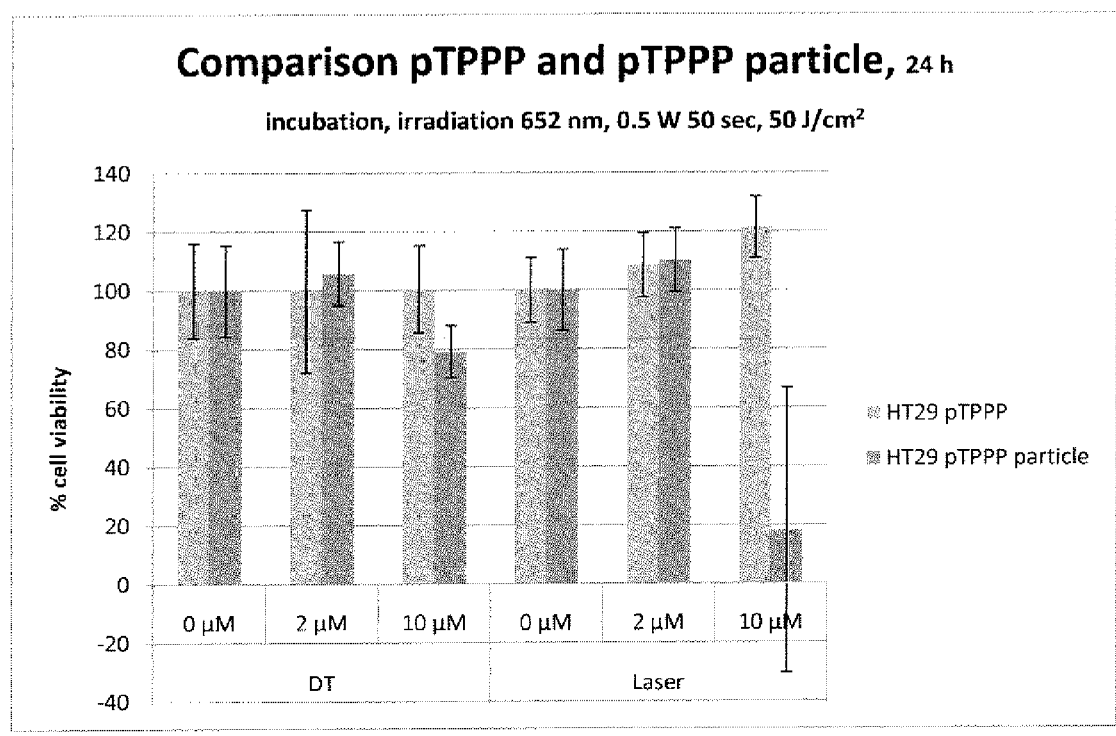
FIG. 7 shows a comparison of the photodynamic effect of the photosensitizer pTPPP in pure form (aqueous solution) and of a calcium phosphate nanoparticle formulation according to the present invention.

As it is obvious from the FIG. 7, the photosensitizer pTPPP exhibits no photodynamic activity if it is applied to the HT29 cell culture in water solution. If on the other hand the photosensitizer is applied in a calcium phosphate nanoparticle formulation, it exhibits a very strong phototoxicity at a concentration of 10 µM.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A nanoparticle pharmaceutical formulation for photodynamic therapy comprising:
   a crystalline or amorphous biodegradable ceramic core with a diameter in the range of 5-1000 nm;
   a therapeutically effective amount of a hydrophobic or hydrophilic photosensitizer; and
   a stabilizing agent;
   suitable for intravenous administration and having improved solubility in physiological solutions;
   wherein said ceramic core is solid or hollow and the material of said core is selected from the group consisting of calcium phosphate and calcium carbonate;
   wherein said hydrophobic or hydrophilic photosensitizer is selected from the group consisting of tetrapyrrole derivatives, phenazinium dyes, phenothiazinium dyes, and xanthene dyes; and
   wherein said stabilizing agent is selected from the group consisting of cationic, non-ionic and anionic polymers.

2. The nanoparticle pharmaceutical formulation according to claim 1, wherein said anionic stabilizing agent are selected from the group consisting of sodium polystyrene sulfonate (PSS) and carboxymethylcellulose (CMC).

3. The nanoparticle pharmaceutical formulation according to claim 1, wherein said cationic stabilizing agent are selected from the group consisting of poly(allylamine) hydrochloride (PAH) and polyethylene imine (PEI).

4. The nanoparticle pharmaceutical formulation according to claim 1, wherein said photosensitizer is selected from the group consisting of porphyrins, chlorins, bacteriochlorins, methylene blue, toluidine blue, safranin, and erythrosine.

5. The nanoparticle pharmaceutical formulation according to claim 4, wherein said photosensitizer is temoporfin (mTHPC).

6. The nanoparticle pharmaceutical formulation according to claim 1, wherein said therapeutically effective concentration of the photosensitizer is from 1 to 500 µM.

7. The nanoparticle pharmaceutical formulation according to claim 6, wherein said therapeutically effective concentration of the photosensitizer is from 1 to 100 µM.

8. The nanoparticle pharmaceutical formulation according to claim 1, wherein said biodegradable ceramic core has a diameter in the range of 50-250 nm.

9. The nanoparticle pharmaceutical formulation according to claim 1, wherein the $Ca^{2+}$ ion of said calcium phosphate or calcium carbonate is substituted in part up to a fully extent by a ion selected from the group consisting of $Mg^{2+}$ ion, $Al^{3+}$ ion, or $Sr^{2+}$ ion.

10. The nanoparticle pharmaceutical formulation according to claim 1, wherein said hydrophobic or hydrophilic photosensitizer is a tetrapyrrole derivative fictionalized with phosphate groups 1 to 4 per molecule.

11. The nanoparticle pharmaceutical formulation according to claim 10, wherein said hydrophobic or hydrophilic photosensitizer is a hydrophilic photosensitizer.

12. The nanoparticle pharmaceutical formulation according to claim 11, wherein said hydrophilic photosensitizer is 5,10,15,20-tetrakis(4-phosphonooxyphenyl)porphine (pTPPP).

13. The nanoparticle pharmaceutical formulation according to claim 1, wherein said nanoparticles are equipped with a targeting ligand selected from the group consisting of an antibody, an antibody fragment, a RGD peptide, and combinations of these.

14. The nanoparticle pharmaceutical formulation according to claim 1, wherein said nanoparticle formulation further comprises a biologically targeting molecule attached to the surface of the nanoparticle.

15. A method of preparation of the nanoparticle pharmaceutical formulation of claim 1, comprising the steps of,
   a. forming inorganic nanoparticles by a continuous precipitation process of inorganic solutions;
   b. adding a stabilizing agent during the precipitation; and
   c. adding a photosensitizer before, during or after precipitation.

16. The method of preparation according to claim 15, wherein said inorganic solution is a calcium solution and a solution selected from the group consisting of phosphate solutions, and carbonate solutions.

17. The method of preparation according to claim 15, further comprising the step of adding a stabilizing agent during the precipitation of the inorganic nanoparticles.

18. The method of preparation according to claim 15, wherein said anionic stabilizing agent are selected from the group consisting of sodium polystyrene sulfonate (PSS) and carboxymethylcellulose (CMC).

19. The method of preparation according to claim 15, wherein said cationic stabilizing agent are selected from the group consisting of poly(allylamine) hydrochloride (PAH) and polyethylene imine (PEI).

20. The method of preparation according to claim 17, further comprising a step of functionalizing said nanoparticles using a layer-by-layer method.

21. The method of preparation according to claim 17, wherein said inorganic nanoparticles are stabilized photosensitizer-loaded calcium phosphate particles.

22. The method of preparation according to claim 15, wherein said inorganic nanoparticle comprises a crystalline or amorphous biodegradable ceramic core with a diameter in the range of 5-1000 nm.

23. The method of preparation according to claim 15, wherein said inorganic nanoparticle comprises a crystalline or amorphous biodegradable ceramic core with a diameter in the range of 50-250 nm.

24. The method of preparation according to claim 15, wherein the $Ca^{2+}$ ion of said calcium phosphate or calcium carbonate can also be substituted in part up to a fully extent by a ion selected from the group consisting of $Mg^{2+}$ ion, $Al^{3+}$ ion, or $Sr^{2+}$ ion.

25. The method of preparation according to claim 15, wherein said hydrophobic or hydrophilic photosensitizer is selected from the group consisting of temoporfin, porphyrins, chlorins, and bacteriochlorins, toluidine blue, methylene blue and safranin, and erythrosine.

26. The method of preparation according to claim 15, wherein said hydrophilic photosensitizer is 5,10,15,20-tetralds(4-phosphonooxyphenyl)porphine (pTPPP).

* * * * *